(12) United States Patent
Gibson et al.

(10) Patent No.: US 7,794,746 B2
(45) Date of Patent: Sep. 14, 2010

(54) PREBIOTIC COMPOSITIONS

(75) Inventors: Glenn R. Gibson, Reading (GB); Sofia Kolida, Reading Berkshire (GB)

(73) Assignee: Nestec S.A., Vevey (CH)

( * ) Notice: Subject to any disclaimer, the term of this patent is extended or adjusted under 35 U.S.C. 154(b) by 235 days.

(21) Appl. No.: 10/721,652

(22) Filed: Nov. 25, 2003

(65) Prior Publication Data

US 2004/0131659 A1 Jul. 8, 2004

(30) Foreign Application Priority Data

Dec. 12, 2002 (GB) ................................ 0229015.3

(51) Int. Cl.
*A61K 47/00* (2006.01)
(52) U.S. Cl. .................................................... 424/439
(58) Field of Classification Search ........................ None
See application file for complete search history.

(56) References Cited

U.S. PATENT DOCUMENTS

| | | | |
|---|---|---|---|
| 5,444,054 | A | 8/1995 | Garleb et al. |
| 5,531,989 | A | 7/1996 | Paul |
| 5,776,887 | A | 7/1998 | Wibert et al. |
| 5,780,451 | A | 7/1998 | DeMichele et al. |
| 5,827,526 | A * | 10/1998 | Dohnalek et al. ........... 424/440 |
| 5,952,314 | A | 9/1999 | DeMichele et al. |
| 6,399,124 | B1 * | 6/2002 | Lesens et al. ................. 426/61 |
| 6,451,584 | B2 | 9/2002 | Tomita et al. |
| 6,468,987 | B1 | 10/2002 | Demichele et al. |
| 2003/0138476 | A1 * | 7/2003 | Van Leeuwen et al. ...... 424/439 |

FOREIGN PATENT DOCUMENTS

| | | |
|---|---|---|
| AU | 718640 | 12/1997 |
| EP | 0 756 828 | 8/1995 |
| EP | 0 834 317 | 6/1996 |
| EP | 1 254 664 | 7/1996 |
| EP | 1 105 002 | 8/1999 |
| EP | 1 010 372 | 12/1999 |
| EP | 1 175 905 | 7/2000 |
| JP | 4311384 | 11/1992 |
| JP | 11302182 | 11/1999 |
| JP | 2002051731 | 2/2002 |
| WO | WO 97/02829 | 1/1997 |
| WO | WO 97/29763 | 8/1997 |
| WO | WO 00/08948 | 2/2000 |
| WO | WO 01/64225 | 9/2001 |
| WO | WO 02/07533 | 1/2002 |
| WO | WO 02/39835 | 5/2002 |
| WO | WO 02/051264 | 7/2002 |

OTHER PUBLICATIONS

Moro et al, "Dosage-Related Bifidogenic Effects of Galacto- and Fructooligosaccharides in Formula-Fed Term Infants," Mar. 2002, Pediatric Gastroenterology and Nutrition, 34, pp. 291-295.*
Boehm et al. , "Supplementation of a bovine milk formula with an oligosaccharide mixture increases counts of faecal bifidobacteria in preterm infants", May, 2002, Atachives of Disease Cildhood, 86, 3, F178-F181.*
Rigo et al., "Growth, weight gain composition and mineral accretion in term infants fed a new experimental formula containing hydrolyses protein, palmitate and prebiotics", 2001, Pediatrika, 21(10), 387-396.*
Walters et al., Effect of a New Mixed-Fibre-Supplemented Enteral Formula on Healthy Volunteers' bowel function, Proc. Nutr. Soc., vol. 56, No. 2, p. 274A (1997)—Abstract.
Green et al., "Short Chain Fatty Acid (SCFA) and Gas Production of Individual Fibre Souces and a Mix Typical to a Normal Diet Using an In Vitro Technique", J. Pediatr. Gastroenterol. Nutr., vol. 26, No. 5, p. 591 (1998)—Abstract.
Duncan et al., "An Investigation of the Effects of a Novel Mixed Fibre Enteral Feed on COlonic Motility", Gastroenterol., vol. 112, p. A725 (1997)—Abstract.
Boehm et al., "Bifidogenic Effect of an Oligosaccharide Mixture in Formula Fed Preterm Infants", Prenatal Neonat. Med., vol. 5, Suppl. 2, p. 77 (2000)—Abstract.
Boehm et al., "Bifidogenic Oligosaccharides in a Preterm Infant Formula", J. Pediatr. Gastro-ent. Nutr., vol. 31, Suppl. 2, p. 26 (2000)—Abstract.
van der Burgt et al., Intestinal Microflora of Chronic Functional Constitipated Children Determined with Fluorescent In Situ Hybridization (FISH); J. Ped. Gastroenterol. Nutr., p. S243 (2000)—Abstract.
Trier et al., "Effects of a Multifibre Supplemented Paediatric Enteral Feed on Gastrointestinal Function", JPGN, vol. 28, No. 5, p. 595 (1999)—Abstract.
Green, "Fibre in Enteral Nutrition", Clin. Nutri., vol. 20, Suppl. 1, pp. 23-39 (2001).
Silk et al., "The Effect of a Polymeric Enteral Formula Supplemented with a Mixture of Six Fibres on Normal Human Bowel Function and Colonic Motility", Clin. Nutri., vol. 20, No. 1, pp. 49-58 (2001).
Green, "Fibre in Enteral Nutrition", SAJCN, vol. 13, No. 4, pp. 150-160 (2000).
Moro et al., "Dosage-Related Bifidogenic Effects of Galacto- and Fructooligosaccharides in Formula-Fed Term Infants", JPGN, vol. 34, pp. 291-295 (2002).

* cited by examiner

*Primary Examiner*—Robert A Wax
*Assistant Examiner*—Bethany Barham
(74) *Attorney, Agent, or Firm*—Gary M. Lobel

(57) ABSTRACT

The present invention concerns nutritional compositions comprising oligosaccharides for controlling inflammatory bowel disease and related disorders, such as diarrhea and constipation.

8 Claims, No Drawings

SEQUENCE LISTING

<160> NUMBER OF SEQ ID NOS: 7

<210> SEQ ID NO 1
<211> LENGTH: 17
<212> TYPE: DNA
<213> ORGANISM: Bacteroides spp.

<400> SEQUENCE: 1
ccaatgtggg ggacctt                                              17

<210> SEQ ID NO 2
<211> LENGTH: 18
<212> TYPE: DNA
<213> ORGANISM: Bifidobacterium spp.

<400> SEQUENCE: 2
catccggcat taccaccc                                             18

<210> SEQ ID NO 3
<211> LENGTH: 19
<212> TYPE: DNA
<213> ORGANISM: Clostridium coccoides- Eubacterium rectale

<400> SEQUENCE: 3
cgguaccuga cuaagaagc                                            19

<210> SEQ ID NO 4
<211> LENGTH: 22
<212> TYPE: DNA
<213> ORGANISM: Clostridium histolyticum

<400> SEQUENCE: 4
aaaggaagau uaauaccgca ua                                        22

<210> SEQ ID NO 5
<211> LENGTH: 21
<212> TYPE: DNA
<213> ORGANISM: E.coli

```
-continued

<400> SEQUENCE: 5
caccgtagtg cctcgtcatc a                                              21

<210> SEQ ID NO 6
<211> LENGTH: 20
<212> TYPE: DNA
<213> ORGANISM: Lactobacillus/Enterococcus spp.

<400> SEQUENCE: 6
ggtattagca sctgtttcca                                                20

<210> SEQ ID NO 7
<211> LENGTH: 16
<212> TYPE: DNA
<213> ORGANISM: Desulfovibrio spp

<400> SEQUENCE: 7
tacggatttc actcct                                                    16
```

PREBIOTIC COMPOSITIONS

The present invention concerns prebiotic compositions comprising of soluble fibres, in particular fructo-oligosaccharides (FOS) and galacto-oligosaccharides (GOS), and their use in the treatment or prevention of gastrointestinal tract disorders, such as inflammatory bowel disease (IBD), diarrhoea and constipation.

Prebiotics are non-digestible food ingredients which have a beneficial effect on health. For a food ingredient to be classified as a prebiotic it must fulfill the following criteria: i) neither be hydrolysed, nor absorbed in the upper gastrointestinal tract, ii) be selectively fermented by one or a limited number of potentially beneficial bacteria commensal to the colon, such as *lactobacilli* and *bifidobacteria*, which are stimulated to grow and/or become metabolically activated, iii) be able to alter the colonic microflora towards a healthier composition, by increasing, for example, numbers of saccharolytic species while reducing putrefactive microorganisms. *Bifidobacteria* are obligate anaerobes that metabolize carbohydrates, mainly to acetic and lactic acids, which are further metabolized systemically. They are thought to play an important role in gut homeostasis, the suppression of putrefactive and pathogenic bacteria, production of some vitamins, activation of intestinal function, assistance of digestion and absorption, as well as the stimulation of the immune response.

Because *bifidobacteria* are susceptible to oxygen and heat, their application in foods has been limited. Therefore, there has been increased interest in prebiotics, which show effectiveness, endure normal food processing and selectively target indigenous beneficial bacteria.

One desirable attribute for prebiotics is the ability to persist towards distal region of the colon. This region of the gut is the site of origin of several chronic disease states including colon cancer and ulcerative colitis. It is thought that the microflora in this region of the gut may play an important role in the onset or maintenance of such disorders. Dietary carbohydrate is the main fermentable substrate in the proximal colon and as this is degraded during bacterial fermentation, protein takes over as the main fermentable substrate in more distal regions. The products of bacterial protein metabolism include toxic and potentially carcinogenic compounds such as amines, ammonia and phenolic compounds.

Constipation is a commonly occurring problem in hospital patients as a consequence of lack of fibre in the diet resulting in increased transit time and reduced faecal mass. Illness, drugs, immobility and reduced fluid intake also contribute to this problem. By supplementing patients with a higher fibre diet via the hospital diet and/or through the use of oral supplements or enteral nutrition, studies have shown an increase in stool weight and bowel frequency.

Inflammatory bowel disease (IBD) is a group of disorders that cause inflammation or ulceration in the small and large intestines. Most often, IBD is classified either as ulcerative colitis or Crohn's disease. IDB may predispose to colon cancer. The aetiology of IBD is unknown, and cannot be cured by current drug therapy. Many factors are implicated, in particular genetic, environmental, immune and microbial.

Ulcerative colitis is an inflammatory reaction usually occurring in the rectum and lower part of the colon, or may affect the entire colon. Symptoms include haemorrhage, bloody diarrhoea, rectal bleeding pain, fever, weight loss, and can also induce complications such as colon perforation, conjunctivitis, abscesses, mouth ulcers, skin lesions. Several studies implicate sulphate-reducing bacteria, such as the genus *Desulfovibrio*, in ulcerative colitis. These bacteria, which reduce sulphate to sulphide, are present in 50% of healthy population but ubiquitous in people suffering from ulcerative colitis (97 to 100%); they increase sulfidogenesis in IBD patients, and induce damage such as impairing butyrate oxidation, compromising the epithelial cell barrier, inducing translocation of bacteria and food antigens and inflammation. Other bacteria may be involved in ulcerative colitis, such as *E.coli*, Helicobacter spp., although their role seems less certain. Ulcerative colitis cannot be cured by current drug therapy but it is managed through the use of anti-inflammatory pharmaceuticals. The drugs which can be used to treat patients with mild or moderate disease, such as sulfasalazine, may induce side effects, like nausea, vomiting, diarrhoea or headache. Corticosteroids may be used in more severely sick patients, but may in particular increase risk of infection. In severe cases, surgery is needed to remove the diseased colon.

Crohn's disease differs from ulcerative colitis because it causes inflammation deeper within the intestinal wall and may occur in any part of the gastrointestinal tract, with the small intestine being the most common site. It is also a chronic condition and may occur at various times over a lifetime.

Irritable bowel syndrome (IBS) is characterised by a combination of persistent and recurrent abdominal pain and irregular bowel habits such as diarrhoea, constipation or both. IBS cannot be cured by current drug therapy.

In recent years, there has been on the part of the consumers an increasing demand of foodstuffs that in addition to having a nutritional value can also have a positive impact upon health. In particular, there is interest in developing functional foods containing prebiotics with extended fermentation times capable of reaching the distal bowel and therein increasing numbers of *bifidobacteria*.

In vivo human studies have shown that dietary addition of fructo-oligosaccharides (FOS) leads to an increase in faecal *bifidobacteria* and is an effective prebiotic. However, high levels of FOS may lead towards excessive gas production in human volunteers and the lowest efficacious amount of FOS should be used in the production of prebiotic foods. There is a need for developing new prebiotic compositions.

Present inventors have surprisingly found that the prebiotic properties of FOS are significantly improved by the presence of galacto-oligosaccharides (GOS) and that the effects of FOS and GOS are more than additive, i.e. a synergistic effect in promoting the growth of beneficial bacteria, such as *bifidobacteria* and *lactobacilli*, has been observed.

As a result of this synergy, it is possible to obtain an equivalent or improved prebiotic effect of FOS at lower dosages. This has the advantage that a powerful prebiotic effect can be achieved in vivo while avoiding the need to ingest any single prebiotic at levels that could induce side effects. In addition, the maximum prebiotic benefit obtainable is superior to that gained from prebiotics individually.

Accordingly, in one aspect the present invention provides compositions comprising FOS and GOS, hereinafter referred to as compositions of the invention.

In another aspect of the invention there is provided a composition according to the invention for use as a medicament or clinical product.

In another aspect of the invention there is provided a use of the compositions of the invention in the manufacture of a medicament, e.g. clinical product, or nutritional composition for treating or preventing gastrointestinal transit (GI) disorders, such as for example IBD, diarrhoea or constipation.

In another aspect of the invention there is provided a use of the compositions according to the invention in the manufacture of a medicament or nutritional composition for the prevention or treatment of chronic gut disorder, e.g. IBD and/or for prolonging the remission periods or ameliorating symptoms or conditions associated with this disorder, such as ulcerative colitis, Crohn's disease and/or colon cancer.

In a further aspect of the invention there is provided a use of the compositions according to the invention in the manufacture of a medicament, e.g. clinical product, or nutritional composition for altering the gut bacterial population towards a healthier composition, e.g. for stimulating the growth and/or the metabolism of beneficial gut bacteria, such as *bifidobacteria* and/or *lactobacilli*, and/or in inhibiting the growth and/or the metabolism of non beneficial gut bacteria, such as *Bacteroides*, coliforms, *Clostridium*, sulphate reducing Bacteria.

The invention further provides a use of the compositions of the invention in the manufacture of a medicament, e.g. clinical product, or nutritional composition for the prevention or treatment of infection by pathogenic gut bacteria.

In another embodiment of the invention, there is provided a use of the compositions according to the invention in the manufacture of a medicament or nutritional composition for the prevention or treatment of IBS or its syndromes.

The intake of dietary fibres, particularly of fructans and/or nondigestible oligosaccharides, increases the density of lactic acid producing bacteria in the gastrointestinal tract and reduces the number of undesirable microbes like Enterobacteriaceae. The latter include several pathogens. Accordingly, intake of dietary fibres such as fructans and/or oligofructose can be used to selectively stimulate the growth of beneficial bacteria in the gastrointestinal tract. The improvement of the ratio beneficial/pathogenic bacteria in turn results in beneficial health effects for the host.

As used herein, the term "soluble fibres" pertains to fibres which are able to undergo fermentation in the colon to produce short chain fatty acids (SCFA).

As used herein, the term "oligosaccharide" refers to saccharide consisting of at least two, up to 20 glycosidically linked monosaccharide units, i.e. having a degree of polymerisation (DP) of 2 to 20, preferably of 2 to 15 monosaccharide units, more preferably of 2 to 10 monosaccharide units, and even more preferably of 2 to 7 monosaccharide units or of 2 to 6 monosaccharide units.

Fructooligosaccharides (also called oligofructose) (FOS) are non digestible oligosaccharides that are members of the inulin subclass of fructans. They occur in nature in many kind of plants, including onions, garlic, shallots, wheat, rye, bananas, asparagus, tomatoes, artichokes, dahlia and chicory root. FOS can be produced enzymatically, through chemical techniques or by extraction from natural substances. Short chain FOS are composed of one to three fructose molecules linked to one molecule of sucrose: their polymerisation degree (DP) is not higher than 6, and they can be synthesised from sucrose through the use of transfructosylating enzymes. Treatment of sucrose with these transfructosylating enzymes results in a mixture of FOS containing 2, 3 or 4 fructose units, such as 1-kestose, nystose and fructosyl-nystose. In vivo human studies have been shown that dietary addition of FOS leads to an increase in faecal *bifidobacteria* and is a very effective prebiotic.

As used herein the term "FOS" encompass FOS and short chain FOS. According to the invention, FOS may comprise between 2 and 20 saccharide units, preferably between 2 to 15 saccharide units, more preferably between 2 to 7 saccharide units and even more preferably between 2 to 6 saccharide units. In one embodiment of the invention, FOS may contain about 95% by weight disaccharides to heptasaccharides, based on the total weight of FOS.

Fructooligosaccharides are commercially available, for example as Actilight 950P®, from Beghin-Meiji industries (France), which contains about 92% by weight FOS, or oligofructose (Raftilose) from Orafti, (Tienen, Belgium), in various grades such as, for example, RAFTILOSE&commat P95, which contains about 95% by weight FOS, composed of chains with a degree of polymerisation ranging from 2 to about 7, typically with a DP of 3.5 to 4.5, and containing about 5% by weight in total of glucose, fructose and sucrose.

Galacto-oligosaccharides (GOS) may comprise di, tri, tetra, penta and hexasaccharides, mainly consisting of galactose as a sugar component, and are formed by the action of beta-galactosidase on lactose. According to the invention, GOS may comprise between 2 and 15 saccharide units, preferably between 2 to 10 saccharide units, more preferably between 2 to 7 saccharide units and even more preferably between 2 to 6 saccharide units. In one embodiment of the invention, GOS may contain about 0 to about 45% of weight disaccharides, preferably about 10 to about 40% of weight disaccharides, more preferably about 20 to about 35% of weight disaccharides, and even more preferably about 33% of weight disaccharides, based of the total weight of GOS. According to the invention, GOS may contain about 0 to about 50% of weight trisaccharides, preferably about 10 to about 45% of weight trisaccharides, more preferably about 20 to about 40% of weight trisaccharides, and even more preferably about 39% of weight trisaccharides, based on the total weight of GOS. According to the invention, GOS may contain about 0 to about 50% of weight tetrasaccharides, preferably about 5 to about 45% of weight tetrasaccharides, more preferably about 10 to about 40% of weight tetrasaccharides, and even more preferably about 18% of weight tetrasaccharides, based of the total weight of GOS. According to the invention, GOS may contain about 0 to about 30% of weight pentasaccharides, preferably about 1 to about 25% of weight pentasaccharides, more preferably about 2 to about 10% of weight pentasaccharides, and even more preferably about 7% of weight pentasaccharides, based of the total weight of GOS.

As used herein the term "GOS" encompasses GOS as hereinabove defined and trans galacto-oligosaccharides, also called tGOS.

GOS is commercially available, for example as Elixor®, from Borculo Domo Ingredients (The Netherlands), which contains about 58% by weight galacto-oligosaccharides, 23% by weight lactose and 19% by weight glucose, as Vivinal® GOS 10 (powder), from Borculb Domo Ingredients (The Netherlands), which contains about 28% by weight galacto-oligosaccharides, 46.5% by weight mono-saccharides and di-saccharides,17.5% by weight protein, 3.1% by weight minerals, 1% by weight fat and 4% by weight moisture, and which is available as a co-spray dried mixture with 50% whey protein concentrate (WPC 35), or as Vivinal GOS (syrup) from Borculo Domo Ingredients, which contains 75% by weight dry matter of which 41% by weight are mono-saccharides and di-saccharides and 59% by weight are GOS.

The amount of FOS and GOS contained in the compositions of the invention may be determined in the light of various relevant factors including the purpose of administration, the age, sex and body weight of individual subject, the form of the compositions of the invention, e.g. a powder or a composition ready-for-consumption, e.g. ready-to-drink composition or instant drink, and the severity of symptoms.

The compositions of the invention may comprise FOS in an amount of at least 0.3 g to about 20 g, preferably from about 0.5 to about 12 g, more preferably from about 0.5 to about 5 g.

According to the invention, the amount of GOS in the compositions of the invention may be comprised between about 0.3 g to about 20 g, preferably from about 0.5 to about 12 g, more preferably from about 0.5 to about 5 g.

FOS will suitably be present in the compositions of the invention, e.g. in solid form, e.g. in powder form, in an amount of from about 0.1 to about 40% by weight, preferably about 0.2 to about 30% by weight, e.g. about 0.5 to about 20% by weight, preferably about 1 to about 15% by weight, even more preferably about 2 to about 12% by weight, based on the total weight of the composition.

The amount of GOS in the compositions of the invention, e.g. in solid form, e.g. in powder form, may be comprised between about 0.1 to about 40% by weight, preferably about 0.2 to about 30% by weight, preferably about 0.5 to about 20% by weight, more preferably about 1 to about 15% by weight, even more preferably about 2 to about 12% by weight, based on the total weight of the composition, e.g. on the total weight of the powder composition.

According to the invention the amount of the FOS and GOS blend in the compositions of the invention, e.g. in solid form, e.g. in powder form, may be comprised between about 0.1 to about 60% by weight, preferably about 0.2 to about 40% by weight, preferably about 0.5 to about 30% by weight, preferably about 1 to about 25% by weight, preferably about 2 to about 20% by weight, even more preferably from about 2% to about 15% by weight, based on the total weight of the composition, e.g. on the total weight of the powder composition.

In another embodiment of the invention, suitable amounts of FOS comprised in ready-for-consumption compositions according to the invention are in the range of up to about 20% by weight, or up to about 15% by weight, for example from about 0.05 to about 20% by weight, e.g. from about 0.1 to about 10% by weight, e.g. from about 0.2 to about 5% by weight, or from about 0.5 to about 3% by weight, based on the total weight of the ready-for-consumption composition.

GOS in ready-for-consumption compositions according to the invention may be in an amount of up to about 20% by weight, or up to about 15% by weight, for example of about 0.05 to about 20% by weight, e.g. of about 0.1 to about 10% by weight, e.g. of about 0.2 to about 5% by weight, e.g. of about 0.5 to about 3% by weight, based on the total weight of the ready-for-consumption composition.

According to the invention, the amount of the FOS and GOS blend in ready-for-consumption compositions of the invention are in the range of up to about 40% by weight, up to about 30% by weight, for example from about 0.05 to about 40% by weight, from about 0.1 to about 30% by weight, from about 0.2 to about 20% by weight, from about 0.5 to about 15% by weight, from about 1 to about 10% by weight, from about 2 to about 5% by weight, e.g. about 25%, e.g. about 20%, e.g. about 10% by weight, e.g. about 5% by weight, based on the total weight of the composition, e.g. the ready-for-consumption composition.

The dose, e.g. daily dose, of FOS, e.g. per serving, may be for example about 0.01 g to about 0.5 g/kg body weight, preferably from about 0.03 g to about 0.3 g/kg body weight, more preferably from about 0.05 g to about 0.2 g/kg body weight, even more preferably from about 0.06 g to about 0.15 g/kg body weight. According to the invention, the dose, e.g. daily dose, of GOS, for instance per serving, may be in the range from about 0.01 g to about 0.5 g/kg body weight, preferably from about 0.03 g to about 0.3 g/kg body weight, more preferably from about 0.05 g to about 0.2 g/kg body weight, and even more preferably from about 0.06 g to about 0.15 g/kg body weight. Suitable dose, e.g. daily dose, of the FOS and GOS blend, e.g. per serving, may be for example about 0.01 g to about 1 g/kg body weight, preferably from about 0.03 g to about 0.6 g/kg body weight, more preferably from about 0.05 g to about 0.4 g/kg body weight, even more preferably from about 0.10 g to about 0.3 g/kg body weight.

Suitable dosage, e.g. daily dosage, of the FOS and GOS blend may be comprised between about 1 and about 20 g, preferably between about 1 and about 15 g, more preferably between about 2 and about 10 g, for example may be of about 20 g, preferably of about 15 g, more preferably of about 10 g, even more preferably of about 5 g.

In one aspect, the invention provides a composition of the invention, wherein the weight ratio FOS/GOS is from about 0.01 to about 50, preferably from about 0.5 to about 20, preferably from about 0.1 to about 10, more preferably from about 0.2 to about 5, even more preferably from about 0.3 to about 3, most preferably from about 0.5 to about 2, even most preferably from about 0.6 to about 1.5. The weight ratio FOS/GOS may be about 1.

The relative proportion of the active ingredients of the compositions of the invention will, of course, vary considerably depending on the particular type of composition concerned, e.g. whether it is a liquid or solid form, or whether it is provided in nutritional form. All indicated proportions and relative weight ranges described herein are accordingly to be understood as being indicative of preferred or individually inventive teaching only and not limiting the invention in its broadest aspect.

According to the invention, the compositions of the invention may further comprise insoluble and/or soluble fibres, such as non-starch polysaccharides, e.g. cellulose, hemicellulose, resistant starch, gums, guar gum, hydrolysed guar gum, e.g. partially hydrolysed guar gum, available for example as Benefibre® (from Novartis Nutrition Corporation), pectin, gum Arabic and mixtures thereof.

The compositions of the invention may also comprise polyunsaturated fatty acids, and in particular cis-polyunsaturated fatty acids, such as n-3 fatty acids and/or n-6 fatty acids, for example alpha-linolenic acid (18:3), stearidonic acid, eicosapentaenoic acid (EPA) (20:5), docosapentaenoic acid (22:5) and docosahexaenoic acid (DHA) (22:6), linoleic acid (18:2), gamma-linolenic acid (18:3), arachidonic acid (20:4), either in free form or in form of an oil or fat, and mixtures thereof. Preferably a combination of eicosapentaenoic acid and docosahexaenoic acid may be used.

The compositions of the invention may also comprise a source of nitrogen, e.g. proteins and/or amino acids, and/or a source of fats, e.g. lipids, and/or a source of carbohydrates. The compositions of the invention may also include vitamins and/or minerals.

In another embodiment of the invention, compositions of the invention may also comprise further oligosaccharides, for example lactulose, xylooligosaccharide (XOS), soybean-oligosaccharide (SOS), isomaltooligoasccharide (IMO), arabinogalactan (ABG), gentio-oligosaccharide, fructans, partially hydrolysed guar gum (PHGG), and mixtures thereof, preferably XOS.

In a further embodiment of the invention the compositions of the invention consist essentially of, or exclusively of, FOS and GOS as described herein.

In one embodiment of the invention, there is provided a nutritional or pharmaceutical composition comprising an oligosaccharide blend consisting of FOS and GOS as hereinabove described, e.g. a blend consisting of FOS comprising 2 to 7 monosaccharide units and GOS comprising 2 to 7 monosaccharide units.

Further components of the compositions according to the invention may include any bioactive compounds or extracts which are known to have health benefits, especially compounds which have a beneficial influence on the gastrointestinal tract, such as glutamine/glutamate or precursors thereof.

The compositions of the invention may also contain one or more additional substances that inhibit bacterial adhesion to epithelial wall of the gastrointestinal tract, including mannans, galacturonic acid oligomers, preferably of natural origin. The composition of the invention may be combined with drugs useful for the treatment of ulcerative colitis, such as mesalamine, sulphasalazine, 5-ASA agents, corticosteroids, such as adrenal steroids, prednisone, hydrocortisone or budesonide; or drugs used against pain, diarrhoea, and infection or IBS, such as a serotonin-4 receptor agonist, e.g. Zelnorm/Zelmac™. For example, the composition of the invention may be provided in the form of a combined pharmaceutical formulation or a kit for separate, sequential or simultaneous administration in conjunction with such medicines as described herein above. These medicines may conveniently be formulated together with the composition of the invention in standard pharmaceutical dosage forms.

In one embodiment of the invention, the compositions of the invention do not comprise a plant species of the Ericaceae family, or a material derived from wheat leaf.

In another embodiment of the invention, the compositions of the invention do not comprise raffinose.

In one aspect of the present invention, the compositions according to the invention can readily be incorporated into pharmaceutical or nutritional formulations, typically nutraceuticals, dietary supplements, medical or functional food and beverage products.

In a further aspect of the invention, the compositions of the invention may be used as a medicament. Accordingly the compositions of the invention may be administered in pharmaceutical form or as a dietary supplement, preferably in combination with at least one pharmaceutically or nutritionally acceptable carrier.

The compositions of the invention in form of dietary means, e.g. supplements, or pharmaceutical formulations may consist exclusively of the compositions of the invention, and optionally pharmaceutically or nutritionally acceptable carriers.

In a yet further aspect of the invention, there is provided a medicament, e.g. clinical product, nutritional or pharmaceutical formulation, for example dietary supplement, comprising the composition of the invention. The medicament, e.g. clinical product, nutritional or pharmaceutical composition of the invention may optionally comprise pharmaceutical acceptable carriers. Further, according to the invention there is provided a combined pharmaceutical preparation for simultaneous, separate or sequential use for treating or preventing GI disorders, e.g. for maintaining and/or restoring the gut microflora, for stimulating the growth or multiplication of beneficial gut bacteria and/or inhibiting the growth or multiplication of non beneficial or pathogenic gut bacteria, for the treatment or prevention of IBD, for prolonging the remission periods or ameliorating symptoms or conditions associated with this disorder, such as ulcerative colitis, Crohn's disease and/or colon cancer, for repressing or prolonging the remission periods on IBD patients and in particular on colitic patients. In another embodiment of the invention, the compositions of the invention, e.g. the combined pharmaceutical preparations, may be used for the prevention or treatment of IBS or its syndromes.

As used herein the term "beneficial gut bacteria" refers to beneficial or potentially beneficial gut bacteria, such as *lactobacilli* and *bifidobacteria*; the term "non beneficial gut bacteria" refers to non beneficial or pathogenic gut bacteria, such as *Bacteroides, clostridia*, coliforms, sulphate reducing bacteria.

According to the invention, the term "nutritional compositions" refers to nutritional formulations and nutritional product, such as nutraceuticals, nutritional or dietary supplements, functional food, beverage products, meal replacement, or food additives.

Such nutritional compositions may be nutritionally complete, i.e. may include vitamins, minerals, trace elements as well as nitrogen, carbohydrate and fatty acid sources so that they may be used as the sole source of nutrition supplying essentially all the required daily amounts of vitamins, minerals, carbohydrates, fatty acids, proteins and the like. Accordingly, the compositions of the invention may be provided in the form of a nutritionally balanced composition, e.g. a complete formula diet or a complete meal, e.g. suited for oral or tube feeding.

Alternatively, the compositions of the invention may be provided as. part of a meal, i.e. a nutritional or dietary supplement, e.g. in the form of a health drink.

It may be desirable to provide the composition of the invention in the form of a low calorie composition, e.g. meal replacement. In this case the nutritional composition, e.g. meal replacement, is preferably low fat, i.e. less than about 10 en %, or substantially fat-free, i.e. less than about 2.5 en % contributed by fat, such as about 2 en % fat, based on the total caloric content of the composition. Suitably, a single serving of a low calorie nutritional composition, e.g. meal replacement, will have a caloric value of less than about 1000 kcal, and preferably between about 200 kcal and about 500 kcal.

Suitable low calorie nutritional composition may include soft drink, such as juice, smoothie or soy-based drink, or dispersed in foods of any sort, such as, dairy bars, soups, cereals, e.g. breakfast cereals, muesli, candies, tabs, cookies, biscuits, crackers, such as a rice crackers, and dairy products, such as milk-shake, yoghurt drink, yoghurts and fruit drinks.

Alternatively, the compositions of the invention may be provided as high calorie compositions, e.g. high calorie dietary supplement or meal replacement, for instance with a caloric value of more than about 400 kcal, preferably more than about 600 kcal, more preferably more than about 800 kcal.

According to the invention, the compositions of the invention, e.g. the high calorie compositions, may be rich in proteins, e.g. may contain more than about 1 en % proteins (i.e. 1 g per 100 kcal), preferably more than about 2 en % proteins, more preferably more than about 4 en % proteins, for example may contain from about 1 en % to about 15en % proteins, preferably from about 2en % to about 10en % proteins, more preferably from about 3en % to about 5en % proteins, based on the total caloric content of the composition.

The compositions of the invention, e.g. the high calorie compositions, may contain fats, e.g. more than about 4 en %, preferably more than 5 en %, more preferably more than 6 en %, even more preferably more than 7 en % and most preferably more than 8 en %, based on the total caloric content of the composition.

In one embodiment of the invention there is provided a composition comprising, e.g. per 100 ml, from about 1 to about 3 g FOS, from about 1 to about 3 g GOS, from about 2 to 20 g proteins, from about 1 to about 30 g carbohydrates, from about 0.5 to about 20 g fats, as well as minerals and vitamins, more preferably about 1.25 g FOS, about 1.25 g GOS, about 9 g proteins, about 22 g carbohydrates and about 9 g fats, as well as minerals and vitamins. Such a composition may be a complete formula diet. Such a composition, e.g. complete formula diet, may be a ready-for-consumption composition.

The compositions of the invention optionally comprise conventional food additives, such as any of emulsifiers, stabilisers, sweeteners, flavourings, colouring agents, preservatives, chelating agents, osmotic agents, buffers or agents for pH adjustment, acidulants, thickeners, texturisers, and so on.

Suitable product formats according to the present invention include solution, ready-for-consumption composition, e.g. ready-to-drink compositions, instant drink, liquid comestibles, like soft drinks, juice, sports drinks, milk drinks, milkshakes, yogurt drinks or soup. In a further embodiment of the invention, the compositions of the present invention may be manufactured and sold in the form of a concentrate, a powder, or granules, e.g. effervescent granules, which are diluted with water or other liquid, such as milk or fruit juice, to yield a ready-for-consumption composition, e.g. ready-to-drink composition's or instant drink.

In a further aspect of the invention, there is provided a use of compositions of the invention as a food additive.

Pharmaceutical compositions, e.g. clinical product, and nutritional compositions of the invention, e.g. dietary supplements, may be provided in the form of soft gel, sachets, powders, syrups, liquid suspensions, emulsions and solutions in convenient dosage forms. In soft capsules, the active ingredients are preferably dissolved or suspended in suitable liquids, such as fatty oils, paraffin oil or liquid polyethylene glycols. Optionally stabilisers may be added.

Oral pharmaceutical or dietary supplement forms may be made by conventional compounding procedures known in the pharmaceutical art, that is, by mixing the active substances together with edible pharmaceutically acceptable solid or liquid carriers and/or excipients, e.g. fillers such as cellulose, lactose, sucrose, mannitol, sorbitol, and calcium phosphates and binders, such as starch, gelatin, tragacanth, methylcellulose and/or polyvinylpyrrolidone (PVP). Optional additives include lubricants and flow conditioners, e.g. silicic acid, silicon dioxide, talc, stearic acid, magnesium/calcium stearates, polyethylene glycol (PEG) diluents, disintegrating agents, e.g. starch, carboxymethyl starch, cross-linked PVP, agar, alginic acid and alginates, colouring agents, flavouring agents, and melting agents. Dyes or pigments may be added to the tablets or dragee coatings, for example for identification purposes or to indicate different doses of active ingredient.

The composition of the invention may be in any form suitable for human administration, and in particular for administration in any part of the gastrointestinal tract. Enteral administration of the compositions of the invention, and preferably oral administration, and administration through a tube or catheter, are all covered by the present invention.

The amount and dosage regimen of the compositions of the invention to be administered is determined in the light of various relevant factors including the purpose of administration, the age, sex and body weight of individual subject and the severity of the subject's symptoms.

The compositions of the invention may be administered under the supervision of a medical specialist, or may be self-administered.

The compositions of the invention, e.g. pharmaceutical or nutritional compositions, e.g. food or beverage incorporating compositions according to the invention can be safely-consumed by anyone, and are especially recommended for mammal, such as humans, e.g. adults, suffering from diarrhoea and/or constipation, or diseases, conditions and symptoms related to IBD, in particular ulcerative colitis, Crohn's disease or colon cancer, or IBS or its syndromes. The compositions of the invention, e.g. nutritional supplements, are particularly recommended for mammals, such as humans, e.g. adults, at risk from diarrhoea, constipation or other chronic gut disorders as hereinabove described, for example malnourished people, hospitalised and long-term care patients, and/or ulcerative colitis patients on remission. The compositions of the invention are particularly suited for malnourished and/or elderly.

In one embodiment of the invention, the invention pertains to a method of treating and/or preventing GI disorders, such as diseases, conditions and symptoms related to chronic gut disorder, e.g. IBD, in particular ulcerative colitis, Crohn's disease, colon cancer or IBS or its syndromes, as hereinabove described, in a mammal, including human, in need of such a treatment, comprising administering to said mammal an effective amount of a composition according to the invention. As used herein, the term "an effective amount" refers to an amount effective to achieve a desired therapeutic effect, such as treating and/or preventing diarrhoea, constipation or diseases, conditions and symptoms related to IBD, in particular ulcerative colitis, Crohn's disease, colon cancer or conditions and symptoms related to IBS as hereinabove described.

In another embodiment of the invention, the compositions according to the invention may be used in the manufacture of a medicament or nutritional formulation for the prevention or treatment of diseases, conditions and symptoms related to chronic gut disorder, e.g. IBD, in particular ulcerative colitis, Crohn's disease, colon cancer, or for the prevention or treatment of IBS or its syndromes as hereinabove described in mammal, including human, or for treating or preventing gastrointestinal transit (GI) disorders, such as diarrhoea or constipation.

In a further aspect, the present invention provides a method for maintaining and/or restoring the intestinal flora, e.g. gut microflora, for altering the gut bacterial population towards a healthier composition, in particular for stimulating the growth and/or metabolism of beneficial gut bacteria, e.g. *bifidobacteria* and/or *lactobacilli*, and/or inhibiting the growth and/or metabolism of non beneficial or pathogenic gut bacteria, e.g. *bacteroides*, *clostridia*, coliforms and/or sulphate reducing bacteria.

In yet another aspect of the invention there is provided a method for the preventing or treating infection by pathogenic gut bacteria.

In a further aspect, the present invention provides a method for preventing and/or treating diseases, conditions and symptoms related to chronic gut disorder, e.g. IBD, in particular Ulcerative Colitis, Crohn's disease, colon cancer, or for prolonging the remission periods on IBD patients, in particular on ulcerative colitis patients.

In yet a further aspect, the present invention provides a method for treating or preventing gastrointestinal transit (GI) disorders, such as diarrhoea or constipation.

The invention further provides a method for preventing or treating IBS or its syndromes as hereinabove described in mammal, including humans.

Dependent on the form of application of the compositions of the invention, i.e. as complete formula diet, e.g. complete meal, or as part of a meal, food additive, drink, sachet, tablet or capsule, the compositions of the invention may be taken once daily to five or six times daily. For patients using the compositions of the invention as a supplement to a normal diet, the daily dose may be 1 or 2 servings per day. For patients receiving compositions of the invention as their entire daily nutritional intake, up to six servings per day may be recommended. The compositions of the invention may be served without restriction to time of day, e.g. together with main meals.

The compositions of the invention may be administered under the supervision of a medical specialist, or may be self-administered.

Optimally, the compositions of the invention, e.g. dietary supplements, are consumed at least once a week or once a day on a regular basis for the duration of patient care and treatment, e.g. until normal bowel movement per week (e.g. 3 to 10) and normal stools (e.g. solid) are recorded, and/or until diarrhoea or constipation decreased or stopped, and/or no more abdominal discomfort, pain, flatulence, bloating is experienced by the patient, and/or no blood or excessive mucus is excreted in stools.

In another embodiment, the present invention relates to a process for the production of the compositions of the invention, wherein such a process comprises intimately admixing the components of the composition of the invention. Such processes are well known to one skilled in the art.

The utility of all the compositions of the present invention may be observed in standard clinical tests in, for example, indications as described hereinabove, for example using dosages of FOS and GOS in the range of about 0.01 to about 1 g/kg body weight/day, preferably from about 0.05 to about 0.5 g/kg body weight/day, or using dosages of FOS and GOS in the range of from about 1 to about 30 g or up to about 30 g per serving, for a mammal, e.g. adult, and in standard animal models. The effect of the compositions of the invention for maintaining and/or restoring the intestinal flora, e.g. for preventing and treating IBD and related diseases or symptoms can be monitored by any of the methods known to one skilled in the art, e.g. analysis of colon content, biopsy analysis, e.g. from the sigmoid/rectal region. The microbial population of healthy individuals and those e.g. with Ulcerative colitis may be compared and the differences in the colonic bacterial populations may be detected e.g. by Fluorescence in Situ Hybridisation (FISH) and/or Denaturing Gel Gradient Electrophoresis (DGGE), Polymerase Chain Reaction (PCR) and 16S rDNA sequence analysis. FISH is a culture independent molecular technique employing 16S rRNA oligonucleotide probes labelled with fluorescent dyes (See Table 1). The FISH method allows visualisation and localisation of entire bacterial cells in situ in environmental samples. It will be appreciated that such a method is readily known to one skilled in the art.

TABLE 1

Oligonucleotide probes used for the characterisation of gut microflora using FISH

| Probe | Sequence | Target genus | Temperature |
|---|---|---|---|
| Bac 303 | 5'-CCAATGTGGGGGACCTT-3' | Bacteroides spp. | 45° C. |
| Bif 164 | 5'-CATCCGGCATTACCACCC-3' | Bifidobacterium spp. | 50° C. |
| Erec 482 | 5'-CGGUACCUGACUAAGAAGC-3' | Clostridium coccoides-Eubacterium rectale group | 50° C. |
| Chis 150 | 5'-AAAGGAAGAUUAAUACCGCAUA-3' | Clostridium histolyticum group | 50° C. |
| Ec 1531 | 5'-CACCGTAGTGCCTCGTCATCA-3' | E. coli | 37° C. |
| Lab 158 | 5'-GGTATTAGCA(T/C)CTGTTTCCA-3' | Lactobacillus/Enterococus spp. | 45° C. |
| Srb 687 | 5'-TACGGATTTCACTCCT-3' | Desulfovibrio spp. | 48° C. |

One human clinical trial is effected as follows:

A randomised double blind study comparing the compositions of the invention, e.g. using dosages of FOS with in the range of about 0.01 to about 1 g/kg body weight/day, preferably from about 0.05 to about 0.5 g/kg body weight/day, more preferably from about 0.1 or 0.15 to about 0.2 g/kg body weight/day and dosages of GOS in the range 0.01 to about 1 g/kg body weight/day, preferably from about 0.05 to about 0.5 g/kg body weight/day, more preferably from about 0.1 or 0.15 to about 0.2 g/kg body weight/day, to a standard nutritional supplement is performed in patients with ulcerative colitis aiming at assessment of the effect on intestinal function, faecal microflora or colonic prebiotic fermentation in a 12 month treatment period. 30 patients may be tested. The following parameters is assessed weekly: stool frequency, presence of blood in stool, excess mucus production, stool consistency, bloating, flatulence and abdominal pain. Faecal microflora is characterised by FISH and the numbers of beneficial species (e.g. *lactobacilli* and *bifidobacteria*) is compared to the numbers of genera associated with the diseased state (e.g. *clostridia, bacteroides* and sulphate-reducing bacteria). The concentration of short-chain fatty acids (acetic, propionic, butyric, lactic and valeric) in the faecal samples is also determined. Study of the total faecal DNA extracts is performed using PCR and DGGE.

The invention will now be further illustrated by the following examples.

EXAMPLE 1

In Vitro Study of the Prebiotic Potential of Several Oligosaccharides and Mixture thereof The Fructooligosaccharides (FOS), used as positive control, is Actilight 950P®, Beghin-Meiji industries, France (containing 92% oligosaccharides), The Galactooligosaccharides (GOS) is Elixor®, FCDF, Netherlands (containing 58% oligosaccharides, 23% lactose, 19% glucose).

The Xylooligosaccharides (XOS) is Xylo-oligo 95P®, Suntory Limited, Japan (containing 91% oligosaccharides).

The Soyaoligosaccharides (SOS) is Soybean Otigosaccharides Syrup, Soya Oligo Japan Inc., Japan (containing 23% oligosaccharides, 21% sucrose, 31% other saccharides).

The Arabinogalactan (ABG) is ClearTrac AG-99®, Larex Inc., USA (containing 95% soluble fibres).

The Acacia gum (AG), also called gummi arabicum, is Fibregume®, Colloides Naturels International, France (containing 85% soluble fibres).

The Wheat germ (WG) is Biogerm PB1®, Multiforsa, Switzerland (containing 32% oligosaccharides, 30% protein, 12% fibres, 7% fat).

The Isomaltooligosaccharides (IMO) is Isomalto 900®, Showa Sangyo Co., Japan (containing 89% oligosaccharides).

1. Method

The prebiotic potential of FOS, GOS, XOS, SOS, ABG, AG, WG and IMO was determined using in vitro faecal batch cultures. Similarly, the prebiotic potential of mixtures of oligosaccharides, namely, FOS+GOS, AG+FOS, FOS+XOS, XOS+GOS and AG+GOS, in equal ratios was investigated in vitro. FOS was used as a positive control, against which the prebiotic nature of the test carbohydrates was compared. Faecal batch cultures using the test compound(s) as sole carbohydrate sources were conducted using faecal inocula from 6 healthy adults who were free of known metabolic and gastrointestinal diseases (e.g. diabetes, ulcerative colitis, Crohn's disease, peptic ulcers, IBS, gastroenteritis and cancer). The samples were collected on site, kept in the anaerobic cabinet and used within a maximum of 5 minutes after collection. A 1:10 dilution in 0.1M anaerobic phosphate buffer (pH 7.4) was prepared and the samples homogenised in a stomacher for 2 minutes.

(a) Batch Cultures 135 ml sterile chemostat medium was maintained under anaerobic conditions (continuous gassing with $O_2$ free $N_2$), at 37° C. in stirred vessels. The culture pH was maintained at 6.7. The carbohydrate sources, 1% weight/volume, were then added. Each vessel was inoculated with a 15 ml fresh human faecal suspension (10% w/v) prepared in anaerobic phosphate buffered saline. Batch cultures were maintained for 24 hours.

(b) Bacterial Enumeration

Samples of the batch culture were taken at 0, 5, 10 and 24 hours of growth. Fluorescent in situ hybridisation (FISH) was used for the bacteriology, with total bacteria, *Bacteroides spp.*, *Bifidobacterium spp.*, *Clostridium perfringens/histolyticum* subgroup and the *Lactobacilli* being enumerated using group specific fluorescently labelled DNA probes targeting 16S rRNA (See Table 1).

2. Results

The results presented and discussed here are the combined results for 6 runs of each different potential prebiotics.

FOS+GOS was selectively and highly fermented by *bifidobacteria* after both 10 and 24 hours of fermentation. The increase was at both points higher than during the fermentation of FOS or GOS alone. Bacteroides numbers decreased slightly. The combination exhibited one of the largest increases of all test substrates in *lactobacilli* during the first 10 hours of fermentation. The increase was not maintained after 24 hours, but numbers stayed above initial levels. Although *clostridia* showed a small increase at 10 hours, numbers dropped after 24 hours below initial levels. A very small decrease in *bacteroides* numbers was observed after 24 h. FOS+GOS was utilised quickly by *bifidobacteria* and *lactobacilli* and increased numbers much higher than FOS or GOS alone. This relatively large increase in *lactobacilli* after 10 hours of fermentation is very important, as prebiotics are usually fermented by *bifidobacteria* causing little if any change in *lactobacilli*. It seems that the combination synergistically increases numbers of the beneficial bacteria.

3. Discussion

Results showed clearly that oligosaccharides are fermented much more selectively by the beneficial bacteria, mainly *bifidobacteria* and *lactobacilli* than the soluble fibres tested in this trial.

The combination FOS and GOS acts synergistically, and enhances surprisingly *bifidobacteria* and *lactobacilli* to higher amounts than when these oligosaccharides were tested alone. The less beneficial bacteria seem not be influenced by the combination towards a reduction in numbers, but rather increased slightly, as compared to both oligosaccharides tested separately. They are especially good prebiotics due to their property to enhance growth selectively. The combination of FOS and GOS showed clearly of all ingredients and combination tested the best prebiotic ranking over the entire fermentation period.

EXAMPLE 2

Nutritional Composition: for 100 g

| | |
|---|---|
| FOS | 1 g |
| GOS | 1 g |
| Hydrolysed guar gum[1] | 0.2 g |
| Glutamine | 1 g |
| eicosapentaenoic acid (EPA) | 0.43 g |
| docosahexaenoic acid (DHA) | 0.28 g |

[1]Benefiber ®, from Novartis Nutrition Corporation.

EXAMPLE 3

Nutritional Composition per 100 g:

The composition is in form of a powder, daily dosage (42 g) should be dissolved in approximativly 200 ml of cold water before consumption.

| | |
|---|---|
| Vivinal ® GOS 10[2] | 42.38 g |
| Actilight 950P FOS[3] | 12.62 g |
| Skimmed milk powder | 21.49 g |
| Whole milk powder | 9.52 g |
| Cocoa aroma | 6.55 g |
| MCT oil | 1.07 g |
| Chocolate flavour | 0.71 g |
| Caramel flavour | 0.19 g |
| Sweet. Saccharin-Na | 0.07 g |
| Vanillin, fine | 0.03 g |

[2]from Borculo Domo Ingredients (The Netherlands), which contains about 28% by weight GOS.
[3]from Beghin-Meiji industries (France), which contains about 92% by weight FOS.

EXAMPLE 4

Ready-to Drink Dietary Supplement, per 100 ml (100 kcal)

| | |
|---|---|
| FOS(4) | 1.25 g |
| GOS(5) | 1.25 g |
| Protein | 9 g |
| Carbohydrates | 21.4 |
| Sucrose | 5 g |
| Lactose | 0.7 g |
| Fats | 8.7 g |
| saturated FA | 0.81 g |
| monounsaturated FA | 4.84 g |
| polyunsaturated FA | 2.54 g |
| Vitamin A | 80 µg |
| Vitamin D | 1 µg |
| Vitamin E | 1 mg |
| Vitamin C | 6 mg |
| Vitamin K | 7 µg |
| Vitamin B1 | 0.14 mg |
| Vitamin B2 | 0.16 mg |
| Vitamin B6 | 0.2 mg |
| Vitamin B12 | 0.14 µg |
| biotin | 7.5 µg |
| folic acid | 20 µg |
| niacine | 1.8 mg |
| panthotenic acid | 0.6 mg |
| Sodium | 60 mg |
| Potassium | 160 mg |
| Calcium | 190 mg |
| Magnesium | 30 mg |
| Phosphorus | 90 mg |
| Chloride | 70 mg |
| Iron | 1.5 mg |
| Zinc | 1.5 mg |
| Copper | 200 µg |
| Molybdenum | 8 µg |
| Manganese | 0.3 mg |
| Chromium | 10 µg |
| Selenium | 6 µg |
| Fluoride | 150 µg |
| Iodine | 15 µg |

(4)from Vivinal GOS from Borculo Domo Ingredients (The Netherlands).
(5)from Raftilose P95 from Orafti (Belgium).

The invention claimed is:

1. A composition comprising a) about 15 g to about 20 g of a fructo-oligosaccharide (FOS) and galacto-oligosaccharide (GOS) blend per 100 mL of composition; (b) each of said oligofructose and oligogalactose are composed of chains with a degree of polymerization ranging from about 2 to about 7; (c) the weight ratio of FOS and GOS is from about 0.5 to about 20; and (d) the FOS and GOS are capable of synergistically promoting the growth of *Lactobacilli*, such that their combined prebiotic property is greater than the sum of their individual prebiotic properties.

2. The composition according to claim 1, wherein said composition provides at least 400 kcal per serving.

3. The composition according to claim 1, wherein the composition comprises more than about 1 en % protein, based on the total caloric content of the composition.

4. The composition according to claim 1, wherein the composition is nutritionally complete.

5. The composition according to claim 1, wherein the composition comprises, per 100 ml: about 9 g proteins, about 22 g carbohydrates and about 9 g fats.

6. The composition according to claim 1, wherein the composition is a ready-for-consumption composition.

7. The composition according to claim 1, wherein the composition further comprises glutamine.

8. A composition comprising glutamine and consisting essentially of about 15 g to about 20 g of a fructo-oligosaccharide (FOS) and galacto-oligosaccharide (GOS) blend per 100 mL of composition, wherein each of said FOS and GOS contains up to 95% by weight of said oligofructose and said oligogalactose that are composed of chains with a degree of polymerization ranging from about 2 to about 7 and wherein the weight ratio of FOS and GOS is from about 0.5 to about 20 and wherein the FOS and GOS are capable of synergistically promoting the growth of *Lactobacilli*, such that their combined prebiotic property is greater than the sum of their individual prebiotic properties.

* * * * *